US006312667B1

(12) United States Patent
Trom et al.

(10) Patent No.: US 6,312,667 B1
(45) Date of Patent: *Nov. 6, 2001

(54) METHODS OF ETCHING HARD TISSUE IN THE ORAL ENVIRONMENT

(75) Inventors: Matt C. Trom, Cottage Grove; Joel D. Oxman, St. Louis Park, both of MN (US)

(73) Assignee: 3M Innovative Properties Company, St. Paul, MN (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/190,717

(22) Filed: Nov. 12, 1998

(51) Int. Cl.⁷ .............................. A61C 5/00; A61C 6/00; A61C 6/08; A61K 7/16; C09K 13/06
(52) U.S. Cl. .......................... 424/49; 433/215; 433/216; 433/228.1; 433/229; 433/226; 106/35
(58) Field of Search .................. 424/49–58; 433/215, 433/216, 228.1

(56) References Cited

U.S. PATENT DOCUMENTS

| | | |
|---|---|---|
| 3,639,574 | 2/1972 | Schmolka et al. . |
| 3,652,420 * | 3/1972 | Hill .................................. 510/116 |
| 4,011,309 * | 3/1977 | Lutz .................................. 424/52 |
| 4,100,271 * | 7/1978 | Krezanoski ........................ 424/78 |
| 4,130,501 | 12/1978 | Lutz et al. . |
| 4,188,373 | 2/1980 | Krezanoski . |
| 4,474,751 | 10/1984 | Haslam et al. .................... 424/78 |
| 4,474,752 | 10/1984 | Haslam et al. .................... 424/78 |
| 4,537,778 | 8/1985 | Clipper et al. . |
| 4,696,757 | 9/1987 | Blank et al. . |
| 4,719,149 | 1/1988 | Aasen et al. ..................... 428/473 |
| 4,774,093 | 9/1988 | Provenchee et al. . |
| 4,795,527 * | 1/1989 | Cohen ............................ 252/79.2 |
| 4,839,156 | 6/1989 | Ng et al. . |
| 4,861,760 * | 8/1989 | Mazuel et al. .................... 514/54 |
| 4,888,168 | 12/1989 | Potts et al. . |
| 4,921,626 * | 5/1990 | Rhodenbaueh ................. 252/79.4 |
| 4,980,152 | 12/1990 | Frazier et al. . |
| 5,000,955 | 3/1991 | Gould et al. . |
| 5,059,417 * | 10/1991 | Williams et al. ................ 424/616 |
| 5,061,183 * | 10/1991 | Nicholson ....................... 433/228.1 |
| 5,071,637 * | 12/1991 | Pellico, I ........................... 424/52 |
| 5,073,363 * | 12/1991 | Pellico, II .......................... 424/52 |
| 5,077,033 | 12/1991 | Viegas et al. . |
| 5,098,303 | 3/1992 | Fischer . |
| 5,122,365 | 6/1992 | Murayama . |
| 5,124,151 | 6/1992 | Viegas et al. . |
| 5,171,564 | 12/1992 | Nathoo et al. . |
| 5,234,342 | 8/1993 | Fischer . |
| 5,252,318 | 10/1993 | Joshi et al. .................... 424/78.04 |
| 5,256,065 * | 10/1993 | Nicholson ..................... 433/228.1 |
| 5,256,396 * | 10/1993 | Piechoth ........................... 424/49 |
| 5,300,295 | 4/1994 | Viegas et al. . |
| 5,340,613 | 8/1994 | Hanzalik et al. . |
| 5,376,006 | 12/1994 | Fischer . |
| 5,376,693 * | 12/1994 | Viechs et al. ..................... 523/106 |
| 5,376,695 | 12/1994 | Schmidt . |

(List continued on next page.)

FOREIGN PATENT DOCUMENTS

| | | |
|---|---|---|
| 0 102 200 A2 | 3/1984 | (EP) . |
| 0 288 420 | 10/1988 | (EP) . |
| 325 267 | 7/1989 | (EP) . |
| 0 535 816 | 4/1993 | (EP) . |
| 545 594 | 6/1993 | (EP) . |
| 612 512 | 8/1994 | (EP) . |
| 0 758 544 A2 | 2/1997 | (EP) . |
| 1 571 832 | 7/1980 | (GB) . |
| 2 170 406 | 8/1986 | (GB) . |
| 59 128330 A | 7/1984 | (JP) . |
| 86/00813 | 2/1986 | (WO) . |
| 91/14650 | 10/1991 | (WO) . |
| WO 97/00275 | 1/1997 | (WO) . |
| 97/11675 | 4/1997 | (WO) . |
| 98/30494 | 7/1998 | (WO) . |
| WO 96/28056 | 9/1996 | (WO) ............................. A43B/7/28 |
| WO 96/02276 | 2/1996 | (WO) ............................. A61K/47/38 |
| WO 96/02577 | 2/1996 | (WO) ............................. C08B/15/00 |
| WO 96/25457 | 8/1996 | (WO) ............................. C08K/9/12 |
| WO 96/06134 | 2/1996 | (WO) ............................. C08L/33/24 |

OTHER PUBLICATIONS

Den–Mat Corporation, "The Innovative Company Behind Rembrandt Products," product information sheets [on–line]. Den–Mat Corporation, 1998–1999 [retrieved on Mar. 13, 2000]. Retrieved from the Internet: <URL:http//www.rembrandt.com/denmat/about.htm> 14 pgs.

Den–Mat product information sheets [on–line]. Den–Mat Corporation, 1998–1999 [retrieved on Mar. 13, 2000]. Retrieved from the Internet: <URL:http://www.denmat.com/main/htm> 10 pgs.

Discuss Dental product information sheets for Professional Whitening Products [on–line]. Discuss Dental [retrieved on Mar. 13, 2000], Retrieved from the Internet: <URL:http://www.discusdental.com/> 13 pgs.

Haywood et al., "Nightguard Vital Bleaching," Quintessence International, vol. 20, No. 3, pp. 173–176 (1989).

Ultradent Online Materials and Procedures Manual [on–line]. Ultradent Products, Inc., 1999 [retrieved on Mar. 13, 2000]. Retrieved from the Internet: <URL:http://www.ultradent.com/> 20 pgs.

BASF Product Literature, "BASF Performance Chemicals Pluronic® & Tetronic® Surfactants," BASF Corporation (1996).

"Surfactants, Pluronic & Tetronic," BASF Product Information Brochure, Mount Olive, New Jersey, 40 pages (1999).

*Primary Examiner*—Shep K. Rose

(57) ABSTRACT

Dental etching compositions are provided that have the capability of undergoing an increase in viscosity in response to an increase in temperature. In a preferred embodiment, the compositions also have the ability to reverse their viscosity in response to a decrease in temperature.

23 Claims, 1 Drawing Sheet

U.S. PATENT DOCUMENTS

| | | |
|---|---|---|
| 5,378,542 | 1/1995 | Hanzalik et al. . |
| 5,401,495 | 3/1995 | Murayama . |
| 5,409,630 * | 4/1995 | Lysy et al. .............. 510/401 |
| 5,409,631 | 4/1995 | Fischer . |
| 5,441,732 | 8/1995 | Hoeg et al. .............. 424/78.04 |
| 5,492,937 | 2/1996 | Bogentoft et al. . |
| 5,575,652 | 11/1996 | Gaffar et al. . |
| 5,631,000 | 5/1997 | Pellico et al. . |
| 5,718,886 | 2/1998 | Pellico . |
| 5,725,843 | 3/1998 | Fischer . |
| 5,746,598 | 5/1998 | Fischer . |
| 5,766,012 * | 6/1998 | Rosenbaum et al. ............ 433/228.1 |
| 5,766,574 | 6/1998 | Christina-Beck et al. . |
| 5,770,105 | 6/1998 | Fischer . |
| 5,814,304 | 9/1998 | Wong et al. . |
| 5,819,988 | 10/1998 | Sawhney et al. . |
| 5,846,570 * | 12/1998 | Barrow et al. .............. 424/616 |
| 5,847,023 * | 10/1998 | Viechs et al. .............. 523/106 |
| 5,851,514 | 12/1998 | Hassan et al. . |
| 5,861,148 * | 1/1999 | Smith .............. 424/78.04 |
| 5,902,568 | 5/1999 | Ryles et al. . |
| 5,928,628 | 7/1999 | Pellico . |
| 6,116,900 | 9/2000 | Ostler . |

\* cited by examiner

METHODS OF ETCHING HARD TISSUE IN THE ORAL ENVIRONMENT

FIELD OF THE INVENTION

This invention relates to dental compositions suitable for etching hard tissue having viscosities capable of responding to a change in temperature. The invention also relates to methods of etching hard tissues by applying the composition directly onto a target area of the substrate.

BACKGROUND

An etchant placed on a hard tissue will dissolve the substrate in such a way as to allow for good mechanical retention of a cured adhesive or other coating which is applied subsequent to the etching treatment. In the dental art, the use of a dental etchant is generally necessary to obtain optimal bonding of a restorative or other material to dentin or enamel. To attain proper etching at the desired location on the hard tissue, it is desirable that the etchant be controllable and slow to flow away from it target site. Thus a high viscosity etchant in the oral environment would be quite useful.

Currently available etchants are provided in seemingly extreme viscosity states. That is, there exist compositions that have very low viscosities as well as compositions that are highly thickened and therefore possess high viscosity. Those with low viscosities are difficult to control and have tendencies to flow away from the target site once it is applied. Compositions with high viscosities are difficult to extrude through a small orifice.

Certain etchant compositions may use thickeners such as fumed silica and polyvinyl alcohols. Problems encountered in using these thickeners include aging, which results in non-homogenous gels which make handling difficult, and shear thinning, which reduces the viscosity of a gel when extruded through an orifice and thinning at elevated temperatures. Thinning can result in a material that drips onto soft tissue causing irritation and damage to the tissue.

SUMMARY OF THE INVENTION

The present invention provides a dental composition suitable for etching hard tissue comprising an acid and a thermally responsive viscosity modifier, capable of undergoing an increase in viscosity in response to an increase in temperature. These compositions also preferably have the ability to reverse their viscosity upon the lowering of temperature.

Compositions of the invention work very well in the oral environment where temperature is generally higher than ambient or the pre-treatment temperature of a composition. This differential in temperature thickens the composition and thus provides a thickened, semi-solid or gel-like composition in the oral environment.

A preferred method of use of the invention comprises applying the composition directly onto the hard tissue. Upon exposure of the composition to the oral temperature, the composition thickens to a semi-solid or gel-like state.

DETAILED DESCRIPTION OF THE INVENTION

Figure 1:
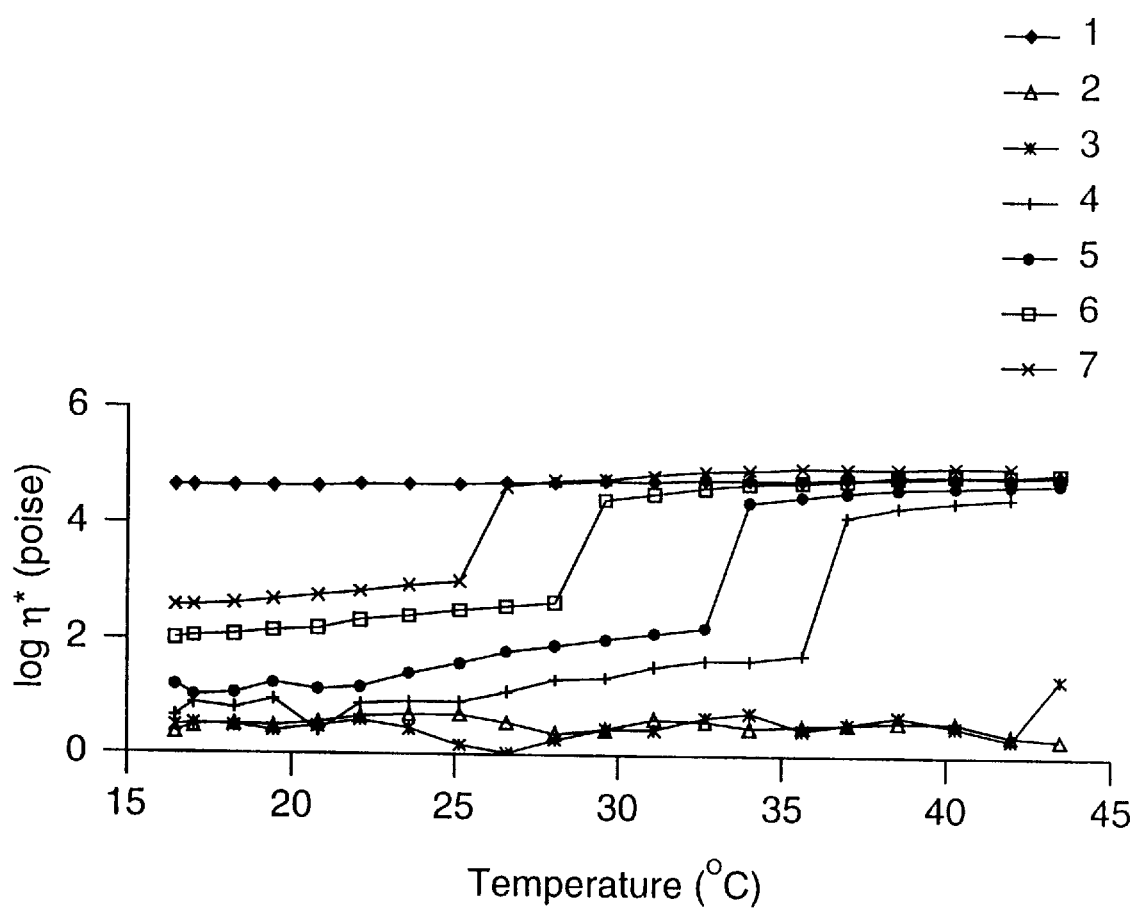
FIG. 1 is a graphic illustration of the viscosity versus temperature data as described in Example 1.

The art of etching hard tissue typically requires etching a target site or controlled areas of several teeth at one time. Current etchant liquids are easy to dispense and apply, but these tend to flow away from the target area of application. Consequently, an etch patch could be larger than desired or, more undesirably, contact with the soft tissue could occur, which can cause sensitivity or irritation. A large etch patch unnecessarily increases the risk of decalcification during treatment. Some compositions have been provided in thickened states to provide less flow and mobility; however, they are often difficult to dispense.

The present invention provides an etching composition in a low viscosity state prior to application onto hard tissue, but which also is highly viscous, thick and controllable at the target site. These compositions are easily dispensed, applied, and manipulated when handled by the user, and are easily controlled upon application to the target site. Because the composition has a low viscosity initially at a pre-treatment temperature, it requires lower syringe extrusion forces to deliver the compositions to the intended site. In turn, this would allow a user the alternative of using a brush or other applicator to apply the etchant. In addition, production of low viscosity compositions may provide easier processing and greater uniformity and consistency.

Compositions of this invention are particularly suitable for use in the intraoral environment where a composition having a pre-treatment temperature at or lower than ambient (room temperature) is applied to a user's hard tissue that is near or at oral temperature of about 30° C. to about 39° C. For certain dental applications, it is preferred that the composition be thermally reversible. In that application, the composition not only has the ability to increase its viscosity at an elevated intra-oral temperatures, but also reverses or decreases its viscosity upon a decrease in temperature.

The capacity of the dental composition to thicken at oral temperatures is a critical feature of the invention, for it is in this property that many of the disadvantages of previous approaches are overcome. The dissipative characteristic of liquid solutions is avoided since the compositions herein experience thickening at the site of treatment. Moreover, the problems of formulation, handling, delivery and application of viscous compositions are overcome since the present compositions may be free-flowing liquids prior to treatment.

A "semi-solid," as used herein, is a material whose physical state is between the solid and liquid state, in which pure or mixed solvent or solution is entrained within a network, and can alternatively be considered a gel. By "pure or mixed solvent and/or solution," as stated herein, it is recognized that a mixture of solvents may be absorbed by the network. Additionally, the solvent may include salts or other additives so as to form a solution, which may also be absorbed or entrained within the network.

"Thickening" as used herein, is where a composition undergoes a substantial increase in the viscosity of the composition. The degree of thickening is dependent on the initial viscosity of the composition.

In a preferred embodiment of the invention, the initial viscosity of the composition may be low enough such that the composition is in a liquid state. Subsequently, upon exposure to a temperature of about near or at oral temperature, the viscosity increases to result in a thickened composition. A viscosity increase in the range of about 10- to 100-fold can be experienced when the initial viscosity is such that the composition is a liquid. Thus, for example, a composition in a liquid state may have a viscosity of about 0–7000 poise. In response to an increase in temperature, the viscosity of the composition can increase to at length about 10,000 poise. Upon the lowering of the temperature, the composition preferably has the ability to reverse its viscosity and return to flow properties of a liquid.

Yet another preferred embodiment of the invention is when the initial viscosity of the composition is at a level at which the composition is in a semi-solid state at pre-treatment temperature (viscosity is at least about 5000 poise), and upon exposure to a higher treatment temperature, the composition transforms into an "ultra-thick" composition or one with a substantially higher viscosity and very low flow characteristics. For compositions having initially high viscosities, the degree of thickening is typically 2- to 5-fold.

The pre-treatment temperature is the temperature at which the composition is subjected to prior to application or treatment. The range for the pre-treatment temperature can be about 5° C. to about 29° C., although there may be certain instances where the temperature may be outside this range. Having a pre-treatment temperature at about 20° C. to 25° C. allows the composition to be easily stored at ambient or room temperature. Alternatively, the compositions of the invention can also be advantageously stored at lower, refrigeration pre-treatment temperatures of about 5° C. to about 10° C. to provide improved stability and shelf life.

The treatment temperature is the temperature which the composition is exposed to during intraoral application. This can be at or near body temperature, or about 30° C. to about 39° C.

In accordance with the invention, the dental composition consists of a water-miscible, physiologically compatible medium which is liquid at ambient temperature below about 30° C. and experiences thickening at oral temperatures above about 30° C. It has been found that a composition having a thickening transition temperature in the range of from about 25° C. to about 40° C. is useful in the practice of the present invention. Preferably, the thickening occurs in a temperature range of from about 25° C. to about 39° C., and more preferably from about 30° to about 35° C.

Compositions of this invention are comprised of a solvent, an acid, and one or more polymeric substances that provide the desired viscosity increase at the desired elevated temperature range in the said composition. Optionally, other adjuvants may be added to the composition. Preferably, the composition of this invention should be physiologically compatible so that no adverse reaction occurs if the etching composition comes in contact with human tissue or fluids.

As used herein, a "thermally responsive viscosity modifier" is one or more polymeric substances that provides the composition or polymeric system the capability of substantially changing its viscosity in response to a change in temperature. Suitable polymeric substances useful as thermally responsive viscosity modifiers include polyoxyalkylene polymers, particularly the polymeric surfactants available under the tradename PLURONIC. This class of polymers is available commercially from BASF Wyandotte Corporation. Other polyoxyalkylene polymers may also be useful as a thermally-responsive composition material.

A preferred dental composition in accordance with this invention comprises an aqueous solution of a selected polyoxyethylene-polyoxypropylene block copolymer. A composition comprising polyoxyethylene-polyoxypropylene block copolymers in which the number of polyoxyethylene units is at least about 50% of the number of units in the total molecule, and the block copolymer having an average molecular weight of from about 1100 to about 15,500 has been found to be particularly useful. It is more preferable that a composition comprises about 70% polyoxyethylene units of the total number of monomeric units in the copolymer and the copolymer has an average molecular weight of about 11,500. PLURONIC F-127 is a material that meets these criteria.

The PLURONIC polymers are closely related block copolymers that may be generically classified as polyoxypropylene-polyoxyethylene condensates that terminate in primary hydroxyl groups. These polymers are formed by the condensation of propylene oxide into a propylene glycol nucleus followed by the condensation of ethylene oxide onto both ends of the polyoxypropylene base. The polyoxyethylene hydrophilic groups on the ends of the base pre-polymer are controlled in length to constitute from about 10% to about 80% by weight of the final polymer.

The PLURONIC polymer series of products may be represented empirically by the formula: $HO(C_2H_4O)_a(C_3H_6O)_b(C_2H_4O)CH$ where a and c are statistically equal.

The concentration of the block copolymers is an important parameter and can be formulated in such a manner corresponding to the other components' concentrations. By adjusting the concentration of the copolymer to accommodate other solutes present in the vehicle, any desired liquid to semi-solid transition temperature in the critical range of above ambient temperature and below body temperature can be achieved. Thus, the principal consideration is the selection of a concentration which, in conjunction with all of the constituents of the total composition, will provide a liquid to semi-solid transition temperature in the required range.

It has been found that a useful block copolymer concentration is from about 5% to about 40% by weight (wt. %) of the composition, particularly from about 17 wt. % to about 26 wt. % of the composition. Excellent results have been obtained using aqueous solutions having from about 17 wt. % to about 29 wt. % of PLURONIC F-127. Increased polymer concentrations may be required in highly acidic systems to affect the same results as in a less acidic system so that, in optimizing the thickening or gelation characteristics for a system, the pH of the solution must be taken into account.

Particularly preferred polymers for the present invention are the PLURONIC F-127 and F-108. These viscosity modifiers are block copolymers of ethylene oxide and propylene oxide. Thickening tendencies of block copolymers increase as ethylene oxide content and total molecular weight increase. Thermally responsive block copolymers have been disclosed in U.S. Pat. Nos. 4,474,751; 4,474,752; 5,441,732; and 5,252,318, as well as the Product Catalog, "BASF Performance Chemicals," all the teachings of which are incorporated by reference herein. These block copolymers offer extremely low toxicity and a high degree of mildness for applications involving human contact.

A preferred solvent for the composition of this invention is water. The concentration of water in the composition can be in the range of from about 30 wt. % to about 90 wt. % of the composition. Preferably, water can exist in the range of about 40 wt. % to about 80 wt. % of the composition. The water used in forming the aqueous solution is preferably purified, as by distillation, filtration, ion-exchange or the like.

Co-solvents may be used, including anhydrous solutions comprising a polyol component such as propylene glycol or polyethylene glycol. Glycerin may also be used as a constituent of the composition.

Acids for use in the present invention can be inorganic or organic acids, and if organic can be monomeric, oligomeric or polymeric. If desired, a precursor to the acid such as an acid anhydride, e.g., 4-Methacryloxyethyl Trimellitate Anhydride (4-META), acid halide (including inorganic acid halides such as Lewis acids, e.g., ferric chloride, and organic acid halides), or ester can be used in place of the acid itself, e.g., to generate the desired acid in situ. Suitable acids include mineral acids, carboxylic acids, sulfonic acids, and phenols, with carboxylic acids, alkylsulfonic acids, arylsulfonic acids, and phosphonic acids being preferred.

The acid has a pKa in water that is less than or equal to that of phenol. Preferably, the pKa of the acid is between about −20 and about +10, more preferably between about −10 and about +5.

The acid can be liquid or a solid; if a solid it should be dissolved in a suitable solvent to enable the acid to wet the hard tissue. Liquid acids can also be dissolved in a suitable solvent, e.g., in order to facilitate wetting. Preferred solvents for the acid are the film former cosolvents discussed in more detail below.

Suitable inorganic acids include hydrobromic acid, hydrochloric acid, nitric acid, phosphoric acid, and sulfuric acid. Suitable organic acids include acetic acid, α-chloropropionic acid, 2-acrylamido-2-methylpropane sulfonic acid, acrylic acid, benzenesulfonic acid, benzoic acid, bromoacetic acid, 10-camphorquinone-sulfonic acid, 10-camphorsulfonic acid, chloroacetic acid, citraconic acid, citric acid, dibromoacetic acid, dichloroacetic acid, di-Hema ester of 1,2,4,5 benzenetetracarboxylic acid, 2,4-dinitrophenol, ethylenediaminetetraacetic acid (EDTA), the mono-, di- and trivalent salts of EDTA, formic acid, fumaric acid, 2-hydroxy-4-methoxybenzophenone-5-sulfonic acid, maleic acid, methacrylic acid, 2-naphthalene sulfonic acid, oxalic acid, p-nitrophenol, phenol, phosphorous acid esters (such as 2,2'-bis(a-methacryloxy-b-hydroxypropoxyphenyl) propane diphosphonate (Bis-GMA diphosphonate), dibutyl phosphite, di-2-ethyl-hexyl phosphate, di-2-ethyl-hexyl phosphite, hydroxyethyl methacrylate monophosphate, glyceryl dimethacrylate phosphate, glyceryl-2-phosphate, glycerylphosphoric acid, methacryloxyethyl phosphate, pentaerythritol triacrylate monophosphate, pentaerythritol trimethacrylate monophosphate, dipentaerythritol pentaacrylate monophosphate, and dipentaerythritol pentamethacrylate monophosphate), pivalic acid, propionic acid, toluene sulfonic acid, tribromoacetic acid, trichloroacetic acid, trifluoroacetic acid, trifluoromethanesulfonic acid, and trihydroxybenzoic acid. Mixtures of such acids can be used if desired.

Other adjuvants can be added to the composition for various purposes. For example, a preferred embodiment of the invention can contain fluoride, a desirable additive in oral composition. Additives may also be included in the composition to promote the stability of the formulation. Anti-microbial agents, anti-fungal agents, and preservatives may be added to the composition to improve shelf-life. The compositions may further include other adjuvants such as medicaments, indicators, dyes, wetting agents, buffering agents, thixotropes, polyols and the like, contingent upon attainment of the desired degree of etching performance and suitability for use on the desired hard tissue. For example, a composition may contain indicators that communicates to the user the degree of etching that has been performed on the hard tissue. The compositions may further include other adjuvants such as fillers, cariostatic agents and flavorings.

In the practice of the present invention, the hard tissues which can be etched include human and animal tissues such as teeth, including the component parts which are enamel, dentin, and cementum. The invention has particular utility for etching dentin, sclerotic dentin, enamel, and cervical enamel. In a preferred method of the invention, the etchant is permitted to stand on the hard tissue for a desired period of time, readily volatile cosolvents are removed therefrom (e.g., by air-drying) to modify the surface of the hard tissue.

Delivery of the composition of the invention may be performed in various methods. One method of delivery of the etching composition is the direct application of the composition onto the hard tissue. This may be done directly from the composition's container or dispenser such as a bottle, vial, syringe, or tube. Alternatively, it can be applied by using a brush to paint or coat the composition onto the hard tissue. The composition is kept on the hard tissue for a desired period to effectuate etching. The length of time the composition is in contact with the hard tissue would depend on the amount of etching desired.

A preferred method of use comprises first etching with the composition of the present invention, followed by an application of a dental material on the tissue such as a sealant or coating, restorative material, adhesive, cement, dental primer or film former. Yet another preferred method is first etching with the composition of the present invention, then followed by an application of a bonding agent for purposes of bonding an orthodontic appliance onto a tooth. The invention enables etching of hard tissue in order to improve the bond strength or durability of a restorative or coating applied thereto.

Hard tissue to which the etchant is applied preferably is first cleaned using conventional methods (e.g., by abrading it with a bur), rinsed (e.g., using water) and dried (e.g., using air). If desired, deep excavations in teeth can be lined with a conventional basing material, (e.g., calcium hydroxide or a glass ionomer cement).

The acid should be allowed to stand on the surface of the hard tissue long enough to provide the desired degree of etching. The standing time will depend upon the particular acid employed, the type of hard tissue and its intended use, and the time available for carrying out the etching procedure. For etching dentin and enamel, standing times less than about 5 minutes, and preferably about 5 seconds to one minute provide very effective etching, although shorter or longer times can be used if desired.

Where the compositions are thermally reversible, the composition can be readily removed from the hard tissue by cooling the material below the liquid to semi-solid transition temperature, thus reversing the thickening effect. This can be accomplished with cool water or other physiologically compatible liquid. Alternatively, the concentrations of the components in the composition may be adjusted and diluted by adding water or other liquid solution. By adjusting the concentrations of the components, the transition temperature is correspondingly adjusted, and thus provides the user the ability to remove the composition even with warm solutions. Water or other liquid solutions may be administered through a rinsing cup, squirt bottle, a liquid dispensing dental tool, or any other liquid dispensing device that can provide solution to the oral environment. Preferably, administering cool or cold water provides a significant decrease in viscosity. Alternatively, the composition may be brushed, wiped, or blown off.

These and other aspects of the invention are illustrated by the following examples which should not be viewed as limiting in scope. Unless otherwise indicated, all molecular weights are number average molecular weights and all ratios, parts and percentages are by weight.

EXAMPLES

Example 1

Etching compositions were made in which the acid used was 3M Etchant Liquid manufactured by 3M Dental Products Division. Sample compositions 3 through 7 were mixed such that the compositions contained 15–30% by weight of PLURONIC F127 (BASF) in 3M Etchant Liquid (3M Co., St. Paul, Minn.).

Complex viscosity versus temperature data were obtained using a controlled strain rheometer ("RDA2", Rheometrics Scientific, Piscataway, N.J.). A parallel plate geometry was used with a plate diameter of 25 mm and a gap of approximately 1 mm. Samples were subjected to an oscillatory strain of 10% applied at a frequency of 1 rad/sec while the temperature was ramped from 15° to 45° C. (3° C./min). The resulting data is shown in FIG. 1.

The compositions 1–7 are phosphoric acid gels of the following types:
Composition #
Comparative 1 3M Dental Etchant Gel containing fumed silica (3M Co.)
Comparative 2 Contains 15.3% PLURONIC F127+84.7% 3M Etchant Liquid
Comparative 3 Contains 18.4% PLURONIC F127+81.6% 3M Etchant Liquid
4 Contains 21.3% PLURONIC F127+78.7% 3M Etchant Liquid
5 Contains 24.0% PLURONIC F127+76% 3M Etchant Liquid
6 Contains 26.5% PLURONIC F127+73.5% 3M Etchant Liquid
7 Contains 28.8% PLURONIC F127+71.2% 3M Etchant Liquid FIG. 1 illustrates the viscosity of each composition in response to temperature. As seen in the Figure, the liquid to gel transition temperature for the compositions containing PLURONIC, as shown by the substantial increase in viscosity in response to temperature increases, is dependent on the concentration of the PLURONIC block copolymer. The silica filled etchant (Comparative Composition 1) maintained a high, consistent viscosity throughout the temperature range.

Example 2

Compositions 2 and 7 were further tested using a laboratory convection oven, heated to a temperature of approximately 45° C.

The concentration of PLURONIC F127 had significant impact on the initial viscosity of the acid etchant gel as well as the temperature at which the acid formed an "immobile gel." An "immobile gel" indicates that the gel did not flow readily under its own weight in small volumes but was still able to be easily manipulated into new positions using hand-held dental instruments. The composition that contained 15.3% PLURONIC F127 had a low initial viscosity similar to that of 3M Etchant Liquid and did not form an immobile gel at approximately body temperature but did form an immobile gel at approximately 45° C. The composition containing 28.8% PLURONIC F127 was a thick liquid when cooled in a refrigerator at approximately 5° C., but was an immobile gel at room temperature of approximately 24° C.

Example 3

An acid composition (gel) containing 24% PLURONIC F127 and 76% 3M Etchant Liquid was placed on a bovine tooth heated to 37° C. The gel was extruded from a syringe as a liquid but formed an immobile gel on contact with the tooth. The gel was left in place for 30 seconds, washed with cold water and dried in the air. There was an obvious difference between the etched and unetched surfaces indicating that the acid gel was effective.

Example 4

An acid gel containing 19.4% PLURONIC F127, 8.1% citric acid (Aldrich, Milwaukee, Wis.) and 72.5% DI water was placed on a bovine tooth heated to 37° C. The gel was extruded from a bottle as a liquid but formed an immobile gel on contact with the tooth. The gel was left in place for 45 seconds, washed with cold water and air dried. There was an obvious difference between the etched and unetched surfaces indicating that the acid gel was effective.

The citric acid and phosphoric acid gels had similar initial viscosity and gel characteristics with significantly different levels of PLURONIC F127. More PLURONIC F127 is required in highly acidic systems to affect the same results as in a less acidic system so that, in optimizing the gelation characteristics for a system, pH of the stock etchant solution must be taken into account.

We claim:

1. A method of etching hard tissue in the oral environment using a dental composition comprising an acid and about 17% by weight to about 40% by weight of a thermally responsive viscosity modifier, wherein the composition is in a low viscosity liquid state at a pre-treatment temperature and a highly viscous state at a treatment temperature that is higher than the pre-treatment temperature, comprising:

applying the composition through an orifice of a syringe onto hard tissue wherein the composition is at the pretreatment temperature and in the low viscosity liquid state prior to being applied onto the hard tissue, allowing the composition to warm to the treatment temperature and increase in viscosity to the highly viscous state wherein the viscosity of the composition at the treatment temperature is at least about 10 times the viscosity of the composition at the pre-treatment temperature, and allowing the composition to remain on the hard tissue for a sufficient time to effectuate etching, whereby said high viscosity dental etchant if pre-gelled or pre-thickened being difficult to extrude through a small orifice, said free flowing low viscosity liquid dental etchant being readily deliverable through a syringe to target sites on oral hard tissue, teeth, enamel, dentin, or cementum intended to be etched where it thickens and forms an immobile gel on the target site which is at or near about 30° C. to about 39° C. where it is kept for the desired period of time to effect etch, said composition being readily removable from the hard tissue by cooling the material below the liquid to semi-solid transition temperature, and thereby reversing the thickening effect.

2. The method of claim 1 wherein the pre-treatment temperature is room temperature.

3. The method of claim 1 wherein the treatment temperature is body temperature.

4. The method of claim 1 wherein the thermally responsive viscosity modifier is a polyoxyalkylene polymer.

5. The method of claim 1 wherein the acid has a $pk_a$ of about less than or equal to that of phenol.

6. The method of claim 1 wherein the acid has a $pk_a$ of about −10 to about +10.

7. The method of claim 1 wherein the acid has a $pk_a$ of about −7 to about +5.

8. The method of claim 1 wherein the acid is selected from the group consisting of polyalkenoic acid, phosphoric acid, maleic acid, citric acid, ethylenediaminetetraacetic acid and salts thereof, and mixtures thereof.

9. The method of claim 1 wherein the composition further comprises a solvent.

10. The method of claim 9 wherein the solvent comprises water.

11. The method of claim 1 wherein the viscosity of the composition at the treatment temperature is about 10 times to about 100 times the viscosity of the composition at the pre-treatment temperature.

12. The method of claim 1 wherein the composition decreases in viscosity upon cooling from the treatment temperature.

13. The method of claim 12 further comprising removing the composition from the hard tissue by cooling the composition from the treatment temperature.

14. The method of claim 13 wherein the composition is cooled by application of a cool liquid.

15. The method of claim 14 wherein the liquid comprises water.

16. A method of etching hard tissue in the oral environment using a dental composition comprising an acid and about 17% by weight to about 40% by weight of a thermally responsive viscosity modifier, wherein the composition is in a low viscosity semi-solid state at a pre-treatment temperature and a highly viscous state at a treatment temperature that is higher than the pre-treatment temperature, comprising:

applying the composition through an orifice of a syringe onto a surface, wherein the composition is at the pretreatment temperature and in the low viscosity semi-solid state prior to being applied onto the surface, allowing the composition to warm to the treatment temperature and increase in viscosity to the highly viscous state wherein the viscosity of the composition at the treatment temperature is at least about 2 times the viscosity of the composition at the pre-treatment temperature, and allowing the composition to remain on the surface for a sufficient time to effectuate etching, whereby said high viscosity dental etchant if pre-gelled or pre-thickened being difficult to extrude through a small orifice, said free flowing low viscosity semi-solid dental etchant being readily deliverable through a syringe to target sites on oral hard tissue, teeth, enamel, dentin, or cementum intended to be etched where it thickens and forms an immobile gel on the target site which is at or near about 30° C. to about 39° C. where it is kept for the desired period of time to effect etch, said composition being readily removable from the surface by cooling the material below the low viscosity semi-solid to highly viscous solid transition temperature, and thereby reversing the thickening effect.

17. The method of claim 16 wherein the pre-treatment temperature is room temperature.

18. The method of claim 16 wherein the treatment temperature is body temperature.

19. The method of claim 16 wherein the viscosity of the composition at the treatment temperature is about 2 times to about 5 times the viscosity of the composition at the pre-treatment temperature.

20. The method of claim 16 wherein applying the composition onto a surface comprises applying the composition onto hard tissue.

21. A method of etching hard tissue in the oral environment using a dental composition comprising an acid and about 17% by weight to about 40% by weight of a thermally responsive viscosity modifier, wherein the composition is in a low viscosity state at a pre-treatment temperature and a highly viscous state at a treatment temperature that is higher than the pre-treatment temperature, comprising:

applying the composition through an orifice onto a surface, wherein the composition is at the pretreatment temperature and in the low viscosity state prior to being applied onto the surface, allowing the composition to warm to the treatment temperature and increase in viscosity to the highly viscous state wherein the viscosity of the composition at the treatment temperature is at least about 10 times the viscosity of the composition at the pre-treatment temperature, and allowing the composition to remain on the surface for a sufficient time to effectuate etching.

22. The method of claim 21 wherein applying the composition onto a surface comprises applying the composition onto hard tissue.

23. The method of claim 21 wherein applying the composition through an orifice comprises applying the composition through an orifice of a syringe.

* * * * *